United States Patent [19]

Yu

[11] Patent Number: 5,089,656

[45] Date of Patent: Feb. 18, 1992

[54] PROCESS FOR THE PREPARATION OF ARYL-SUBSTITUTED PROPIONIC ACID ESTERS

[75] Inventor: Lin-Chen Yu, Wilmington, Del.

[73] Assignee: Himont Incorporated, Wilmington, Del.

[21] Appl. No.: 555,225

[22] Filed: Jul. 18, 1990

[51] Int. Cl.$^5$ ............................................. C07C 69/76
[52] U.S. Cl. ..................................................... 560/75
[58] Field of Search .................................... 560/75

[56] References Cited

U.S. PATENT DOCUMENTS

| | | | |
|---|---|---|---|
| 3,247,240 | 4/1966 | Meier | 560/75 |
| 3,285,855 | 11/1966 | Dexter et al. | 560/75 |
| 3,364,250 | 1/1968 | Dexter et al. | 560/75 |
| 3,840,585 | 10/1974 | Yamada et al. | 560/75 |
| 4,228,297 | 10/1990 | Haeberli et al. | 560/75 |
| 4,529,809 | 7/1985 | Irving et al. | 560/75 |
| 4,547,585 | 10/1985 | Yamonaka et al. | 560/75 |
| 4,659,863 | 4/1987 | Lester | 560/75 |

OTHER PUBLICATIONS

A. A. Volod'kin, et al., —The Reaction Mechanism of the Alkylation of 2,6-Di-Tert-Butyl Phenol by Methyl Acrylate in the Presence of the 2,6-Di-Tert-Butyl Phenolate of Potassium and Alkali, polymer Degradalios & Stability, 26(1989) 89-100.

Primary Examiner—Paul J. Killos

[57] ABSTRACT

Disclosed is a process for the preparation of aryl-substituted propionic acid esters having the formula:

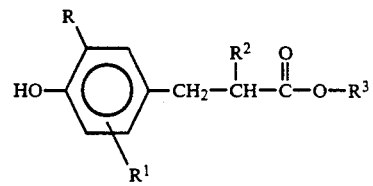

wherein R and $R^1$ are a $C_1$-$C_{12}$ linear or branched alkyl, a $C_5$-$C_{12}$ cycloalkyl, a $C_6$-$C_{12}$ aryl or a $C_7$-$C_{12}$ alkaryl or aralkyl, $R^2$ is hydrogen or a $C_1$-$C_{20}$ linear or branched alkyl and $R^3$ is a $C_1$-$C_{20}$ linear or branched alkyl, a $C_5$-$C_{12}$ cycloalkyl, a $C_6$-$C_{12}$ aryl or a $C_7$-$C_{20}$ alkaryl or aralkyl, and may be the same or different, which comprises forming a reaction mixture of a phenol, at least one base catalyst and an acrylate, in the presence of a complexing agent effective in increasing the rate of reaction, wherein (i) substantially all of the side-product is removed from said reaction mixtrue prior to the addition of the complexing agent and (ii) all or substantially all of the acrylate is added at once to the reaction mixture. The process results in higher yields of the desired product, in a shorter period of time, with a reduction of undesirable by-products.

17 Claims, No Drawings

PROCESS FOR THE PREPARATION OF ARYL-SUBSTITUTED PROPIONIC ACID ESTERS

FIELD OF THE INVENTION

This invention relates to a process for the preparation of aryl-substituted propionic acid esters in higher yields in a shorter period of time.

BACKGROUND OF THE INVENTION

Aryl-substituted propionic acid esters, such as, methyl 3-(3,5-dialkyl-4-hydroxyphenyl)propionates used as antioxidants for plastics, rubber and other polymers, have been prepared by various methods in the prior art. For example, U.S. Pat. Nos. 3,247,240, 3,285,855 and 3,364,250 disclose preparing methyl 3-(3,5-dialkyl-4-hydroxyphenyl) propionates by reacting a 3,5-dialkyl-4-hydroxybenzene with an acrylate in the presence of a base catalyst with or without a solvent. The addition of the methyl acrylate in the above processes is over a period of approximately 20 minutes, but the conversion rate is very slow, from about 6 to 72 hours in the presence of a solvent and at least 3 hours without a solvent.

In U.S. Pat. No. 3,840,855 disclosed is a process for producing an alkyl ester of 3-(3,5-di-t-butyl-4-hydroxyphenyl)propionic acid by reacting 2,6-di-t-butylphenol with an alkyl acrylate in the presence of a catalytic amount of a complex metal hydride with or without a solvent. As in the processes of the above-mentioned patents, the conversion rate is extremely slow, from about 28 to 42 hours to obtain less than 92% yield.

The process disclosed in U.S. Pat. No. 4,529,809 reacts a stoichiometric excess of an olefinic ester with a sterically hindered phenol in the presence of a base catalyst with or without a solvent, wherein the reaction time ranged from 11 to 23 hours with reported yields of 32 to 99%.

U.S. Pat. No. 4,547,585 discloses forming methyl 3-(3,5-di-tert-butyl-4-hydroxyphenyl)propionate, an intermediate product, by reacting an alkyl acrylate with 2,6-di-t-butylphenol in the presence of an alkaline catalyst and preferably a solvent, such as t-butyl alcohol. In this process unreacted acrylate must be removed and the reaction time is from 2 to 10 hours.

In an attempt to minimize the formation of undesirable by-products, U.S. Pat. No. 4,228,297 discloses a process wherein the methyl acrylate is gradually added over a 2 hour period to the phenol compound in the presence of an alkaline catalyst with or without an aliphatic alcohol or dipolar aprotic solvent. Preferably an aliphatic alcohol, such as isopropyl alcohol, is used. However, once all of the acrylate is added an additional 3-4 hours of mixing is necessary to complete the reaction and then the excess acrylate must be removed before acidifying the reaction mixture. The ester was reported in yields of 84% and 87%.

U.S. Pat. No. 4,659,863 discloses an improved process for preparing methyl esters of hindered phenol derivatives by reacting a hindered phenol with methyl acrylate in the presence of an alkaline catalyst and a reaction rate increasing portion of a solubilizing agent such as DMSO. The methyl acrylate can be added by rapid addition, which is stated to be from 15 to 60 min., to the reaction mixture and unreacted acrylate is removed after completion of the reaction.

SUMMARY OF THE INVENTION

It has been unexpectedly found that aryl substituted propionic acid esters can be prepared in a shorter period of time with improved conversion, higher purity and minimum formation of undesirable by-products, by removing substantially all of the side-product prior to adding the complexing agent and adding all or substantially all of the acrylate at once to the reaction mixture.

Accordingly, the present invention provides an improved process for the preparation of aryl-substituted propionic acid esters comprising forming a reaction mixture of a phenol, at least one base catalyst and an acrylate, in the presence of a complexing agent effective in increasing the rate of reaction, where substantially all of the side-product is removed prior to the addition of said complexing agent and all or substantially all of the acrylate is added at once to the reaction mixture. Greater than 92% conversion is obtained within 3 minutes after all of the acrylate has been added.

As used in the present invention, the term "side-product" refers to those products, individually or collectively, other than the phenoxide intermediate, which results from the reaction of the phenol and the base catalyst. The term "by-product", as used in the present invention refers to those products, individually or collectively, other than the aryl-substituted propionic acid esters, which result from the reaction of the phenoxide anion and the acrylate.

DETAILED DESCRIPTION OF THE INVENTION

In the present invention the process for the preparation of aryl-substituted propionic acid esters of the formula:

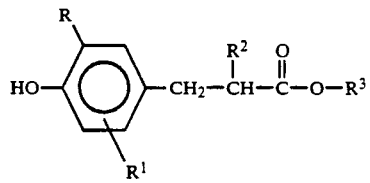

wherein R and R¹ are a $C_1$–$C_{12}$ linear or branched alkyl, a $C_5$–$C_{12}$ cycloalkyl, a $C_6$–$C_{12}$ aryl or a $C_7$–$C_{12}$ alkaryl or aralkyl, $R^2$ is hydrogen or a $C_1$–$C_{20}$ linear or branched alkyl and $R^3$ is a $C_1$–$C_{20}$ linear or branched alkyl, a $C_5$–$C_{12}$ cycloalkyl, a $C_6$–$C_{12}$ aryl, or a $C_{7-20}$ alkaryl or aralkyl, and may be the same or different, comprising (a) forming a reaction mixture of a phenol of the formula:

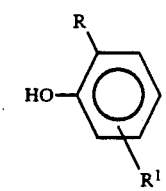

and at least one base catalyst, thereby forming in said reaction mixture a phenoxide intermediate and side-product, (b) removing substantially all of said side-product from the reaction mixture and adding the complexing agent, and (c) adding at once all or substantially all of an acrylate of the formula:

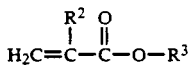

to the reaction mixture of (b).

The phenol reactants of the invention are phenols of the formula:

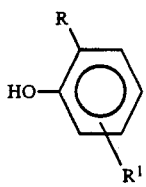

wherein R and $R^1$ are as defined above. Preferably, the phenols are hindered phenols wherein $R^1$ is R as defined above attached to the ring ortho of the hydroxy group. Most preferred are hindered phenols wherein R is a branched alkyl having 4 carbon atoms and $R^1$ is a branched alkyl having 4 carbon atoms attached to the ring ortho of the hydroxyl group, such as 2,6-di-tert-butylphenol. Other suitable phenol reactants include 2-methyl-6-tert-butylphenol, 2,5-di-tert-butylphenol, 2,6-dibenzylphenol, 3,6-di-tert-butylphenol, 2,6-diisopropylphenol and the like.

The acrylate reactants useful in the present invention are of the formula:

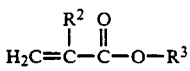

wherein $R^2$ and $R^3$ are as defined above. Suitable examples are methyl acrylate, ethyl acrylate, isopropyl acrylate and methyl methacrylate. Preferred is methyl acrylate.

The acrylate is used in amount of from 1 to 1.2 moles per mole of phenol employed in the present invention. The preferred range is from 1.05 to 1.15 moles of acrylate per mole of phenol.

The base catalyst used in the present invention is an alkali metal catalyst such as alkali metal hydroxides, alkali metal alkoxides, alkali metal amides and alkali metal alkyl amides. Alkali metals for the base catalyst include lithium, sodium and potassium. Examples of the base catalyst used in the present invention are lithium hydroxide, sodium hydroxide, potassium hydroxide, potassium methoxide, sodium methoxide, lithium methoxide, potassium ethoxide, sodium ethoxide, lithium ethoxide, potassium tert-butoxide, sodium tert-butoxide, n-butyllithium, phenyl potassium, phenyl sodium, potassium amide, lithium diisopropyl amide and mixtures thereof. Preferred are potassium tert-butoxide and a mixture of potassium tert-butoxide and sodium methoxide. A suitable amount of base catalyst used in the process of this invention is from about 5 to 100 mole percent based on the amount of phenol reacted. Preferably, the base catalyst is used in an amount of from about 15 to 60 mole percent and most preferably, from 15 to 30 mole percent based on the amount of phenol reacted.

In accordance with the present invention the reaction is carried out in the presence of a complexing agent which is a polar aprotic organic compound and believed to increase the nucleophilicity of the phenoxide. The complexing agent used in the present invention must be capable of complexing with the metal ion of the base catalyst and it must have sufficient polarity to dissolve the particular ingredients employed at the reaction temperature used. Examples of suitable complexing agents are polar aprotic solvents such as N-methylpyrrolidinone (NMP), dimethylformamide (DMF), N,N,$N^1$,$N^1$-tetra-methylethylenediamine (TMEDA) 1,3-dimethyl-2-imidazolidinone (DMI), dimethylpropylene urea (DMPU) and tris[2-(2-methoxyethoxy)ethyl]amine (TDA-1). Dimethylsulfoxide (DMSO), hexamethylphosphoramide (HMPA) and crown ethers, such as 18-crown-6 can also be used. However, HMPA is toxic and may leave impurities in the final products making them unacceptable for use in contact with food, medicines, pharmaceuticals and other materials which are eaten, taken orally or intravenously or topically applied. The crown ethers are highly toxic and, thus, would have the same limitations as the HMPA compound. The preferred complexing agent is N-methylpyrrolidinone. An effective amount of complexing agent used in the present invention is from 20 to 70 mole percent per mole of phenol, preferably 30 to 65 mole percent.

According to the process of this invention, a reaction mixture of the phenol and at least one base catalyst is formed. The reaction mixture is heated to a reaction temperature of about 140° C. to 200° C., wherein a phenoxide intermediate and side-product are formed, and substantially all of the side-product is removed from the reaction mixture. By "substantially all" is meant that at least 95% of the side-product is removed.

The side-product formed during the formation of the phenoxide intermediate product will be an alcohol, water, ammonia, alkane, benzene, amine or mixtures thereof depending on the particular base catalyst or mixture thereof used. For example, the use of a metal alkoxide will give an alcohol side-product and a mixture of a metal alkoxide and a metal hydroxide will give a mixture of alcohol and water as side-products.

Removal of the side-product from the reaction mixture containing the phenoxide intermediate prior to adding the complexing agent is critical. When the side-product is present, it is believed to slow down the regeneration of the phenoxide intermediate by participating in the reaction.

After substantially all of the side-product has been removed, the complexing agent is added to the reaction mixture. The mixture is cooled to from about 110° to 185° C. and all or substantially all of the acrylate is added at once to the reaction mixture.

The addition of the acrylate to the reaction mixture may be carried out in one step, whereby all of the acrylate is added at once, or in two steps, whereby substantially all of the acrylate is added at once and then approximately 2 to 5 minutes later the remaining portion of the acrylate is added. When the addition is in two steps, the amount of acrylate added in the first step must be a 1:1 ratio of acrylate to phenol and the excess acrylate is added in the second step. The one-step method of addition is preferred.

In the process of the present invention all of the acrylate is consumed, therefore unlike the prior art processes, an additional step to remove any unreacted acylate is not necessary.

The reaction mixture is then neutralized with an acid and the product is recovered. Such acids include glacial acetic acid or 5 to 10% diluted hydrochloric acid or sulfuric acid. Preferred is glacial acetic acid.

The temperature range for carrying out the reaction is from about 110° C. to about 200° C., preferably from 140° to 185° C. The temperature of the reaction mixture typically drops slightly when the acrylate is added but then rises approximately 20°-30° C. due the exothermic nature of the reaction.

The present invention will be illustrated in greater detail with reference to the examples of the invention set forth below.

EXAMPLE 1

To a four neck round bottom flask, equipped with a mechanical stirrer, a three-way stopcock, a thermometer and a reflux condenser connected to a cold trap and an oil bubbler, were charged, under nitrogen atmosphere and at room temperature, 45.8 g (0.22 moles) 2,6-di-t-butylphenol and 7.48 g (0.067 moles) potassium t-butoxide. The reaction mixture was heated to 165° C. and t-butanol was removed from the reaction mixture by nitrogen purging and collected in the cold trap. After approximately 10 minutes substantially all of the t-butanol had been removed, 6.4 ml (0.067 moles) N-methylpyrrolidinone were added and stirring continued. Next the reaction mixture, while stirring, was cooled down to 120° C. over a 5 minute period. Then 21 ml (0.23 moles) methyl acrylate were added all at once. The temperature dropped to 105° C. then rose to 139° C. in approximately 2 minutes. When the reaction was completed, the reaction mixture was cooled to about 90° C. and acidified with 4 ml of glacial acetic acid. Then the acidified mixture was diluted with a solution of 40 ml methanol and 8 ml water, allowed to cool to room temperature and the product was filtered. 64.6 g of methyl 3-(2,6-di-t-butyl-4-hydroxyphenyl)propionate was obtained.

The progress of the reaction was monitored by withdrawing aliquot samples from the reaction mixture at 3, 5 and 22 minute intervals after the addition of all of the acrylate and analyzed by gas chromotography. The reaction times, percent conversion, purity and yield are illustrated below in Table 1.

TABLE 1

|  | Reaction Time* | | |
| --- | --- | --- | --- |
|  | 3 min. | 5 min. | 22 min. |
| Conversion (%) | 95.20 | 98.26 | 98.86 |
| Purity (%) | 98.47 | 97.91 | 97.44 |
| Yield (%) | 93.74 | 96.21 | 96.33 |

*Amount of time after which all of the acrylate has been added.

EXAMPLE 2

To a four neck round bottom flask, equipped with a mechanical stirrer, a three way stopcock, a thermometer and a reflux condenser connected to a cold trap and an oil bubbler, were charged, under nitrogen atmosphere and at room temperature, 45.8 g (0.22 moles) 2,6-di-t-butylphenol, 2.49 g (0.022 moles) potassium t-butoxide and 2.40 g (0.044 moles) sodium methoxide. The reaction mixture was heated to 160° C. and t-butanol and methanol were removed from the reaction mixture by nitrogen purging and collected in the cold trap. After substantially all of the alcohols had been removed, approximately 10 minutes, 6.4 ml (0.067 moles) N-methylpyrrolidinone were added and stirring continued. The reaction mixture, while stirring, was cooled to 146° C. and 20 ml, (0.23 moles), methyl acrylate were added. The temperature dropped to 136° C. and rose to 160° C. in approximately 1 minute. Thereafter, approximately 4 minutes, an additional 1 ml of methyl acrylate was added. When the reaction was completed, the mixture was acidified with 4 ml glacial acetic acid. Then the acidified mixture was diluted with a solution of 40 ml methanol and 8 ml water, allowed to cool to room temperature and the product was filtered. Obtained was 64.2 g methyl 3-(2,6-di-t-butyl-4-hydroxyphenyl)propionate. Aliquot samples were withdrawn from the reaction mixture at various intervals and analyzed by gas chromotgraphy as in Example 1. The reaction times, conversion, purity and yield percentages are reported in Table 2.

COMPARATIVE EXAMPLE 1

Example 2 was repeated except that the alcohol was not removed from the reaction mixture of 2,6-di-t-butyl-4-hydroxyphenyl, potassium t-butoxide and sodium methoxide and the reaction was carried out in the absence of N-methylpyrrolidinone at a temperature of 111° C. The results are reported in Table 2.

COMPARATIVE EXAMPLE 2

Example 2 was repeated except that the reaction was carried out in absence of N-methylpyrrolidinone at a temperature of 156° C. The results are reported in Table 2.

COMPARATIVE EXAMPLE 3

Example 2 was repeated except that alcohol was not removed at a temperature of 146° C. The results are reported in Table 2.

TABLE 2

|  | Reaction Time* | | | | | |
| --- | --- | --- | --- | --- | --- | --- |
|  | 3 min. | 6 min. | 10 min. | 15 min. | 30 min. | 45 min. |
| Example 2 | | | | | | |
| Conversion (%) | 92.51 | | 96.25 | 96.30 | | |
| Purity (%) | 97.64 | | 97.27 | 96.85 | | |
| Yield (%) | 90.32 | | 93.62 | 93.27 | | |
| Comp. Example 1 | | | | | | |
| Conversion (%) | | | | 87.86 | 91.37 | 95.71 |
| Purity (%) | | | | 98.53 | 99.53 | 98.27 |
| Yield (%) | | | | 86.56 | 90.94 | 94.06 |
| Comp. Example 2 | | | | | | |
| Conversion (%) | | | | 91.97 | 91.38 | 90.48 |
| Purity (%) | | | | 96.46 | 96.23 | 96.85 |
| Yield (%) | | | | 88.72 | 87.94 | 87.63 |
| Comp. Example 3 | | | | | | |
| Conversion (%) | | 90.99 | 93.31 | 93.11 | 92.86 | 92.88 |
| Purity (%) | | 98.53 | 97.62 | 97.20 | 97.16 | 96.65 |
| Yield (%) | | 89.66 | 91.09 | 90.51 | 90.22 | 89.77 |

*Amount of time after which all of the acrylate has been added.

In Example 2 of the invention, wherein the alcohols were removed and a complexing agent was used, over 92% conversion was obtained in 3 minutes after all of the methyl acrylate had been added. In Comparative Example 1, wherein no alcohol was removed and in the absence of a complexing agent, only about 88% conversion was obtained in 15 minutes. Comparative Example 2, wherein the alcohols were removed, but no complexing agent was used, about 92% conversion was obtained in 15 minutes. Even though the complexing agent was present in Comparative Example 3 where alcohol was not removed, only about 91% conversion was obtained in 6 minutes.

The aryl-substituted propionic acid esters produced by the process of the present invention are obtained in high yields, substantially free of undesirable by-products and in a shorter period of time. They may be used for stabilization of organic materials or as chemical intermediates to the production of known antioxidants for plastics, rubber and other polymers.

Other features, advantages and embodiments of the invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

I claim:

1. A process for the preparation of aryl-substituted esters of the formula:

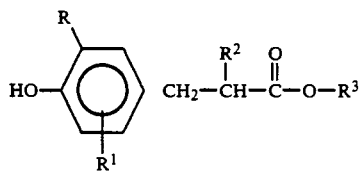

wherein R and $R^1$ are a $C_1$–$C_{12}$ linear or branched alkyl, a $C_5$–$C_{12}$ cycloalkyl, a $C_6$–$C_{12}$ aryl or a $C_7$–$C_{12}$ alkaryl or aralkyl, $R^2$ is a hydrogen or a $C_1$–$C_{20}$ linear or branched alkyl and $R^3$ is a $C_1$–$C_{20}$ linear or branched alkyl, a $C_5$–$C_{12}$ cycloaklyl, a $C_6$–$C_{12}$ aryl, or a $C_1$–$C_{20}$ alkaryl or aralkyl, and may be the same or different, consisting essentially of (a) forming a reaction mixture of a phenol of the formula:

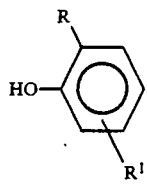

wherein R and $R^1$ are as defined above, and at least one base catalyst in a catalytic amount sufficient to form a reaction product comprising a phenoxide intermediate and a side-product and while heating said reaction mixture at a temperature sufficient to remove the side-product during the formation of the phenoxide intermediate, (b) adding to said phenoxide intermediate an effective amount of an aprotic solvent to increase the rate of reaction and then (c) adding to (b) an acrylate of the formula:

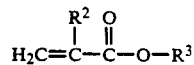

wherein $R^2$ and $R^3$ are as defined above, wherein all or substantially all of said acrylate is added at once.

2. A process according to claim 1, wherein said acrylate is methyl acrylate, ethyl acrylate, methyl methacrylate or isopropyl acrylate.

3. A process according to claim 1, wherein said acrylate is methyl acrylate.

4. A process according to claim 1, wherein said phenol is 2,6-di-t-butylphenol, 2-methyl-6-t-butylphenol, 2,5-di-t-butylphenol, 2,6-diphenylphenol or 2,6-di-benzylphenol.

5. A process according to claim 1, wherein said phenol is 2,6-di-t-butylphenol.

6. A process according to claim 1, wherein said base catalyst is selected from the group consisting of alkali metal alkoxides, alkali metal hydroxides, alkali metal amides, alkali metal alkyl amides and mixtures thereof.

7. A process according to claim 6, wherein said base catalyst is potassium methoxide, sodium methoxide, potassium t-butoxide, sodium t-butoxide, potassium hydroxide or a mixture of potassium t-butoxide and sodium methoxide.

8. A process according to claim 1, wherein said base catalyst is potassium t-butoxide.

9. A process according to claim 1, wherein said aprotic solvent is selected from the group consisting of N-methylpyrrolidinone, hexamethylphosphoramide, N,N,$N^1$,$N^1$-tetra-methylethylenediamine, dimethylsulfoxide, dimethylformamide, crown ethers, 1,3-dimethyl-2-imidazolidinone dimethylpropylene urea and tris[2-(2-methoxyethoxy)ethyl]-amine.

10. A process according to claim 9, wherein said complexing agent is N-methylpyrrolidinone.

11. A process according claim 1, wherein the reaction temperature is from about 110° C. to 200° C.

12. A process according to claim 1, wherein said base catalyst is present in the amount of from 5 to 100 mole percent per mole of phenol.

13. A process according to claim 8, wherein said base catalyst is present in the amount of from 15 to 30 mole percent per mole of phenol.

14. A process according to claim 1, wherein said aprotic solvent is present in the amount of from 20 to 70 mole percent per mole of phenol.

15. A process according to claim 10, wherein said aprotic solvent is used in the amount of from 30 to 65 mole percent per mole of phenol.

16. A process according to claim 15, wherein said acrylate is added all at once to (b).

17. A process according to claim 15, wherein substantially all of said acrylate is added to (b) and then the excess acrylate is added.

* * * * *